United States Patent [19]
Han et al.

[11] Patent Number: 6,037,369
[45] Date of Patent: Mar. 14, 2000

[54] COMPOUNDS OBTAINED FROM SALVIA SPECIES HAVING ANTIVIRAL ACTIVITY

[75] Inventors: Myun K. Han, Silver Spring; Paul Lee, Phoenix, both of Md.

[73] Assignee: Georgetown University School of Medicine, Washington, D.C.

[21] Appl. No.: 09/104,363

[22] Filed: Jun. 25, 1998

[51] Int. Cl.[7] .................. A01N 65/00; A61K 39/385; A61K 35/78
[52] U.S. Cl. .................. 514/532; 514/533; 514/544; 514/548; 514/568; 514/570; 514/571; 514/574; 424/195.1
[58] Field of Search .................. 424/195.1; 514/568, 514/570, 571, 574, 532, 533, 543, 544

[56] References Cited

U.S. PATENT DOCUMENTS

| | | | |
|---|---|---|---|
| 5,178,865 | 1/1993 | Ho et al. .................. | 424/195.1 |
| 5,346,695 | 9/1994 | Nonoyama et al. .................. | 424/78.08 |

OTHER PUBLICATIONS

Chemical Abstract 107:233142, "Active principles of *Salvia plebia*", Aug. 1987.

*Primary Examiner*—Frederick Krass
*Attorney, Agent, or Firm*—Burns, Doane, Swecker & Mathis, LLP

[57] ABSTRACT

The instant invention provides compositions containing molecules having at least one moiety from β(3,4-dihydroxyphenyl) lactic acid and/or caffeic acid which are found in extracts from genus Salvia, said moieties being of the formula:

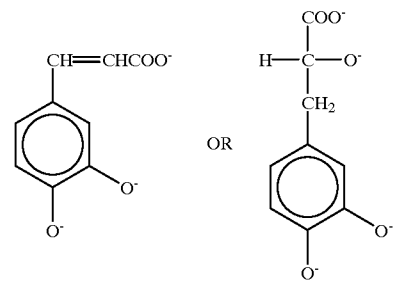

said active agents having a molecular weight of at least 190 daltons. A class of preferred agents are those which are conjugated to form dimers and larger polymers containing said moieties. The agents of the invention may be administered in pharmaceutically acceptable carriers systemically or locally.

14 Claims, No Drawings

COMPOUNDS OBTAINED FROM SALVIA SPECIES HAVING ANTIVIRAL ACTIVITY

FIELD OF THE INVENTION

This invention is related to the use of active agents obtained from extracts of the genus Salvia which are conjugates of molecules having at least one moiety from β-(3, 4-dihydroxyphenyl) lactic acid and/or caffeic acid.

BACKGROUND OF THE INVENTION

The Salvia Miltiorrhiza (SM) plant has long been used in traditional Chinese medicine for treatment of cardiovascular and hepatic diseases. The SM plant has several components which may be extracted. Components of the root have been extracted initially with ethanol followed by extraction with cold water (SM(1)) or with hot water (SM(2)). Both fractions extracted in water have shown antiviral activity. A fraction extracted with ethanol has not shown such activity. The SM(1) and SM(2) extracts have shown minimal toxicity in animals.

Retroviruses possess the ability to reverse the normal flow of genetic information from genomic DNA to mRNA. Although retroviruses are from a clearly defined and relatively homogeneous viral genus, they have been historically subdivided into three taxonomic groupings, primarily on the basis of the pathologic consequences of infection. The oncovirus subgroup includes retroviruses that have the ability to cause neoplastic disease in the infected host as well as several related, yet apparently benign viruses. Lentiviruses cause slow, chronic diseases that generally, although not always, lack a neoplastic component. Members of the spumavirus subgroup cause a marked foamy cytopathic effect in tissue culture. They have yet to be clearly associated with any human or animal disease.

Retroviral replication initiates with the intracytoplasmic penetration of the virion core, a process mediated by the specific interaction of the viral envelope glycoprotein with a specific cell surface receptor. Subsequently, a virion-associated RNA-dependent DNA polymerase transcribes the single-stranded RNA genome into a double-stranded linear DNA proviral intermediate (reverse transcription). Integration protein (integrase) specifically recognizes both ends of the viral DNA and removes two nucleotides from the 3'-ends (3'-donor processing). The processed viral DNA and integrase then migrate to the nucleus, where a viral integrase covalently links the retroviral genome to host chromosomal DNA (strand transfer), thereby forming the retroviral provirus.

The emergence of human immunodeficiency virus type (HIV) as an important human pathogen has led to a resurgence of scientific interest in retroviruses. In particular, scientific evidence indicates that the simple life cycle delineated above is not a completely accurate description of the replication cycle of all the members of this viral genus. For example, HIV-1 encodes no fewer than six gene products in addition to the characteristic retroviral Gag, Pol, and Env, and these are translated from a novel set of singly spliced and multiply spliced viral mRNA species. At least two of these additional proteins, termed Tat and Rev, act in trans to directly regulate HIV-1 gene expression. Therefore, the steps between penetration and proviral integration appeared quite similar for both MLV (murine leukemia virus) and HIV-1, although postintegration events were found to be significantly more complex in the latter. More recently, it has become evident that HIV-1 is merely one of a whole class of animal retroviruses that are now referred to as complex retroviruses. Retroviruses belonging to this complex retroviruses included all lentiviruses, spumaviruses, as well as HTLV-1 and related viruses (Table 1).

TABLE 1

Major taxonomic divisions among retroviruses

| Catagory | Subgroup | Prototype | Other examples |
|---|---|---|---|
| Simple retroviruses | C-type retroviruses group A | RSV | ALV, ASV |
| | C-type retroviruses group B | MLV | FeLV, MSV, SNV, REV, SSV |
| | B-type retroviruses | MMTV | |
| | D-type retroviruses | MPMV | SRV-1 |
| Complex retroviruses | Lentiviruses | HIV-1 | HIV-2, SIV, visna virus, FIV, |
| | T-cell leukemia viruses Spumaviruses | HTLV-1 | EIAV HTLV-II, STLV, BLV |
| | | HSRV | SFV, BFV |

Abbreviations: RSV, Rous sarcoma virus; ALV, avian leukemia virus; ASV, avian sarcoma virus; FeLV, feline leukemia virus; MSV, murine sarcoma virus; SNV, spleen necrosis virus; REV, reticuloendotheliosis virus; SSV, simian sarcoma virus; MMTV, mouse mammary tumor virus; MPMV, Mason-Pfizer monkey virus; SRV-1, simian retrovirus type 1; STLV, simian T-cell leukemia virus; BFV, bovine foamy virus The importance of HIV-1 as a human pathogen has led to its being the major focus of research into lentivirus replication and gene regulation. Indeed, HIV-1 may be viewed as the prototype of not only the lentivirus subgroup but also, more broadly, complex retroviruses in general.

With respect to the development of anti-viral drugs, there are numerous attractive targets to inhibit the retrovirus life cycle (reverse transcriptase, protease, and integrase). To date, of the numerous compounds that have already been identified and approved for marketing by the FDA for HIV only reverse transcriptase and protease inhibitors have been identified.

Recent studies have demonstrated that combinatorial therapy against reverse transcriptase (RT) and protease can eliminate a majority of the HIV viruses in T lymphocytes. Unfortunately, the small fraction of remaining viruses mutate and continue to replicate even in the presence of these drugs. High rates of replication, viral sequence mutation, and rapid turnover of the viral population are typical traits of retroviruses. These traits are even more striking in the case of HIV-1.

Despite the significant progress that has been made in studying the molecular mechanisms of HIV, current anti-HIV chemotherapies have many shortcomings including toxic effects and the induction of resistant strains of virus after relatively short treatment periods. As a result, these drugs lack needed long term benefits necessary for complete treatment or prevention of HIV-infection.

Currently used inhibitors of reverse transcriptase and protease, chemically complex molecules, are enormously expensive. Current estimates indicate that the typical HIV-1 positive patient will spend anywhere from $12,000–$20,000 per year. The 90% of people infected with HIV reside in the developing world, therefore, and even a majority of those in industrialized countries, could not possibly have access to these agents. Therefore, it is apparent that more economically feasible approaches must be sought.

SUMMARY OF THE INVENTION:

The instant invention provides compositions containing molecules having at least one moiety from β(3,4-dihydroxyphenyl) lactic acid and/or caffeic acid which are found in extracts from genus Salvia, said moieties being of the formulae:

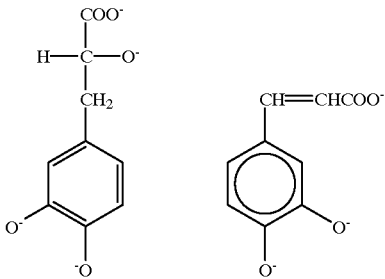

said active agents having a molecular weight of at least 190 daltons. A class of preferred agents are those which are conjugated to form dimers and larger polymers containing said moieties.

The agents of the invention may be administered in pharmaceutically acceptable carriers systemically or locally.

DETAILED DESCRIPTION OF THE INVENTION

This invention uses an alternative approach to develop drugs that are derived from plant extracts. These active agents inhibit retroviral integration, an essential step in the retrovirus lifecycle. The steps involved in proviral integration appear quite similar for both simple and complex retroviruses. There are significant similarities found in structural and functional properties among all types or classes of retroviral integrases studied to date. Because of this commonality of mechanism, an inhibitor of retroviral integrase will inhibit a wide range of organisms such as human immunodeficiency virus (HIV), simian immunodeficiency virus (SIV), Feline Immunodeficiency Virus (FIV), Feline Leukemia Virus (FeLV), Murine leukemia virus (MLV), Rous Sarcoma Virus (RSV), Bovine Immunodeficiency Virus (BIV), Human T-Cell Leukemia virus (HTLV). In addition to these retroviruses, the active agents of the invention may be used as inhibitors against integrase-like proteins to inhibit replication other viruses such as the Hepatitis B virus (HBV).

Preparation Extracts from S.M. and S.Y. Extracts

Plant extracts of S.M. and S.Y. were made. The various fractions of plant extracts were obtained by the following procedure:

Step 1

Dried S.Y. was boiled in Milli-Q $dH_2O$ (18.0 mOhm/cm) and concentrated to a final density of 1.30 g/ml. The extract was then diluted 1:5 with $dH_2O$, centrifuged at 8,000 rpm for 90 min at 25° C. in a GS-3 rotor. The pellet was discarded and the supernatant was saved. To this supernatant a one tenth volume of 1.0 N HCl solution is added to make a final concentration of 0.1 N HCl. This product was incubated overnight at 25° C. The solution is centrifuged at 8,000 rpm for 90 min at 25° C. in a GS-3 rotor and the resulting pellet was then washed with 95% ethanol followed by filtration through a 0.2 μm filter system. This was repeated until the wash solution becomes clear. The pellet was then dried in the filtration unit at room temperature followed by incubation at 70° C. oven overnight. The powder was resuspended in $dH_2O$ at a 1:5 (w/w) ratio of pellet to water. The resulting product was then centrifuged at 25,000 rpm for 30 min at 25° C. in a Ti45 rotor. The supernatant was discarded and the resulting pellet resuspended in 50% ethanol (50% methanol was also used).

Step 2

The resuspended solution was filtered to remove the insoluble materials.

Step 3

The filtered solution was concentrated to one-fifth (1/5) of the original volume. This step resulted in precipitation of the mixture. The pellet was washed with distilled water. The washed pellet was then freeze-dried overnight.

Step 4

Dried powder obtained from step 3 was dissolved in 50% methanol. The solution was centrifuged to remove any insoluble materials. The supernatant solution was applied to a Sephadex LH-20 column equilibrated with distilled water. The column was washed extensively with distilled water and was eluted with the following solutions: 15% methanol in water (v/v), 30% methanol with 1% acetic acid in water (v/v), 40% methanol in water (v/v), 50% methanol in water (v/v), 75% methanol in water (v/v), and 100% methanol. The fraction eluted with 50% methanol in water was concentrated and applied to HPLC reverse column (Ultrasphere ODS, 4.6×250 mm, 5μM), which was equilibrated with 10% methanol and 0.1% formic acid. The column was eluted with a 25 minute gradient of 10% methanol/0.1 % formic acid and 100% methanol/0.1% formic acid at 1 ml/min. Compounds were detected by monitoring the absorbance at 275 nm.

Step 5

Molecular mass of each fraction eluted from the HPLC reverse column was analyzed by mass spectroscopic method. The mass spec. identified the following compounds:

|     | MW  | Compounds |
| --- | --- | --- |
| 1.  | 180 | Caffeic acid (#1) |
| 2.  | 198 | D-(3,4-dihydroxyphenyl)lactic acid (#2) |
| 3.  | 359 | Rosemarinic acid (#3) |
| 4.  | 387 | Derivative of rosemarinic acid (#4) |
| 5.  | 494 | 2-(3,4-dihydroxyphenylethenyl)caffeic acid (#5) |
| 6.  | 521 | Derivative of 5 (#6) |
| 7.  | 717 | Lithospermate B (#7) |
| 8.  | 739 | Magnesium lithospermate B (#8) |
| 9.  | 853 | Combination of rosemarinic acid and 2-(3,4-dihydroxyphenylethenyl)caffeic acid (#9) |
| 10. | 987 | Dimer of 2-(3,4-dihydroxyphenylethenyl)caffeic acid (#10) |

Compounds are of the formula:
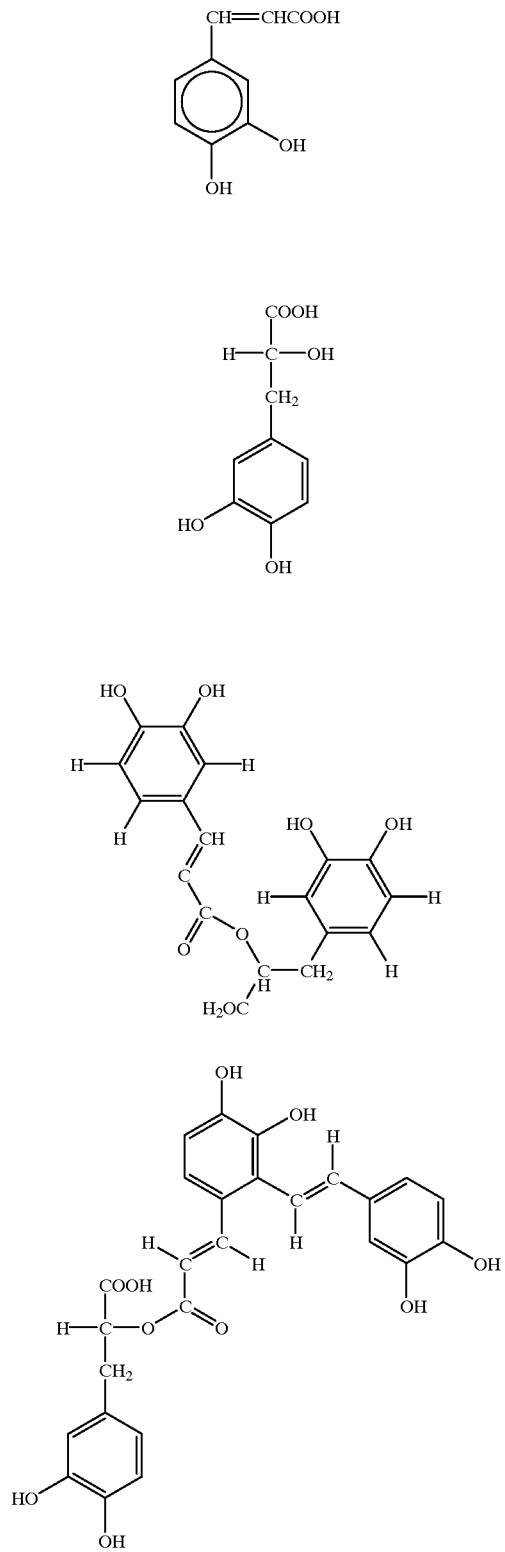
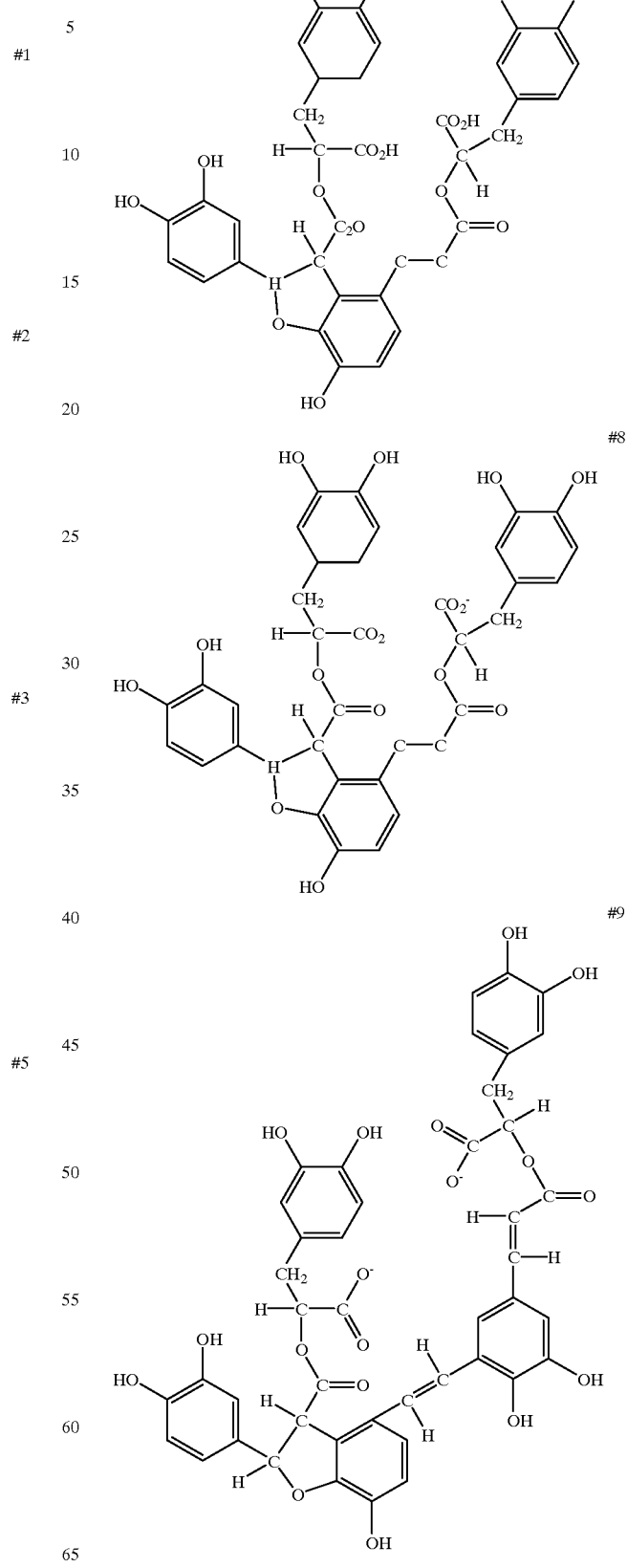

1. Efficacy of Viral Inhibition
   In vitro HIV-1 Integrase Assay
   In vitro assays to monitor the activity of HIV-1 integrase have been developed. These assays utilize purified recombinant HIV-1 integrase and oligonucleotide substrates which represent the LTR ends of the viral DNA. The functional significance of data obtained from the in vitro assays relies on the assays reflecting the actual functional events which occur in vivo. Both fluorometric (Lee et al. (1995) *Analytical Biochemistry* 227, 295–301) and radioactive assays have been developed which improve upon the previously published in vitro assay (Lee et al., (1995) Biochemistry 34, 10205–10214; Lee et al., (1995) Biochemistry 34, 10215–10223). In addition, we have modified the enzyme preparation, which has improved the quality of the HIV-1 integrase sample (Lee and Han (1996) Biochemistry 35, 3837–3844; Lee et al. (1997) Biochemistry). These modifications in the in vitro assay and sample preparation have been improved for to better reflect the events which occur in vivo. Therefore, the results from the in vitro assay are very useful predictors of viral infectivity when searching for potential inhibitors against integrase.

In another evaluation, the activity of the various extract fractions in inhibiting HIV-1 integrase activity was determined. The extract fractions were first dissolved in the appropriate volume of 0.1% $NH_4OH$ (w/v) to make the final concentration 15 mg/ml. These samples were then centrifuged at 10,000 rpm for 30 min. If a pellet was formed the supernatant was removed, the pellet was dried down and then redissolved in 0.1% $NH_4OH$. The resulting solution is the stock solution of the extract fractions. From this stock, the following dilutions were made: 1:10, 1:50, 1:100, 1:200, 1:300, 1:400, 1:500, 1:600, 1:700, 1:800, 1:900, 1:1000, 1:2000, 1:3000, 1:4000, 1:5000, and 1:10,000. 1 µl of each of these dilutions were added to each reaction mixture which corresponds to a final concentration of 75, 15, 7.5, 3.75, 2.5, 1.875, 1.5, 1.25, 1.07, 0.9375, 0.833, 0.75, 0.375, 0.25 0.1875, 0.15, 0.075 µg/ml, respectively. Testing was then carried out as previously described (Lee et al., (1995) Biochemistry 34, 10205–10214; Lee et al., (1995) Biochemistry 34, 10215–10223; Lee and Han (1996) Biochemistry 35, 3837–3844).

To determine the IC 50 and IC 90 of each fraction, the gel was exposed to phoshorimager screening and the percent cleavage determined by the Molecular Dynamics Phosphorimager. The % inhibition was determined by subtracting % cleavage of each fraction from the % cleavage of the positive control and dividing this value by the % cleavage of the positive control. The results demonstrated that the active agents had $IC_{50}$ of 0.2–1.2 µg/ml and $IC_{90}$ of 2.5–3.5 µg/ml in the culture media. In the live mammal, blood concentration of up to 100× that level may be tolerated and beneficial.

b.) In vivo FIV model
   The Feline Immunodeficiency Virus (FIV) model is an accepted animal model for studying drugs for use against HIV infection. FIV is a T cell-trophic lentivirus isolated from felines. FIV resembles HIV biologically and biochemically, which includes high homology between FIV and HIV integrase. FIV infected cats develop Feline Acquired Immunodefeceincy Syndrome (FAIDS) which is similar to full-blown AIDS in humans.

FIV Model in Cells In Vitro
   The Crandell-Reese Feline Kideny (CrFK) cell line is susceptible to FIV infection and supports viral replication. CrFK cells are an effecient means for producing virus and assaying for FIV infection. Although FIV is not cytopathic for FIV infected CrFK cells, diagnostic assays are availble for screening for FIV infection in tissue culture. Studies have demonstrated the efficacy of S.Y.

Determination of ED50

Agents of the invention were tested for protection of CrFK cells from FIV infection. In triplicate, CrFK cells were plated at a density of $1 \times 10^5$ cells/T25 flask. Following a 24 hr incubation for cell attachment and growth, solutions of compounds were applied to the cell cultures for 24 hr. The solutions are made by dissolving the active agents of the invention in phosphate buffer, pH 8 at a concentration of 100 mg/ml, which was then centrifuged at 25,000 rpm for 30 min at 25° C. in a Ti45 rotor. The supernatant solution was removed and three 1 ml aliquots are dried down by centrifugation under an open vacuum for determining the concentration of the solution. The active agent is further diluted down to 2 mg/ml, filtered through a 0.2 µm acetate cellulose filter, and the concentration determined by determining the mass of the dried solute compared to the tared control.

The results demonstrate that the active agents had an $ED_{50}$ range between 0.1 and 1.0 µg/ml and an $ED_{90}$ range between 0.2 and 2.5 µg/ml in preventing FIV infection of CrFK cells.

Compositions of the invention may be administered in pharmaceutically acceptable carriers. Compositions should be administered in sufficient dosage to obtain a blood concentration of 10 nM to 1000 nM. However, in some instances it is necessary to administer doses to obtain concentration of up to 10000 nM in the blood. The more active agents may be effective at blood concentration of as low 1 nM.

Compositions of the invention may be administered orally, systemically or topically. Compositions for oral administration may by be administered in liquid form or as tablets or capsules. For parenteral administration, carriers such as saline, glucose, phosphate buffered saline, and the like may be used. For administration to the central nervous system, compositions may be administered into the cerebral spinal fluid. For intrathecal administration, carriers for parenteral administration, particularly carriers such as glucose in water or saline are appropriate. The compositions may also be prepared in liposomes to enhance transfer across membrane barriers. Of course, compositions for parenteral use, including compositions for intravenous, intramuscular, subcutaneous or intrathecal administration, will be provided in sterile solutions. Compositions may be prepared for transdermal administration via patches. Solvents which are also used for administration of hydrophobic compounds may also be used for this purpose such as DMSO or oils which cross the dermal barrier.

What we claim is:
   1. A method for treating a viral infection by administering to a patient suffering from or at increased risk to suffer from said infection a composition which is a Salvia extract, said extract containing a viral-inhibiting effective amount of an active agent comprising a conjugate containing at least one of each of the moieties of the formulae:

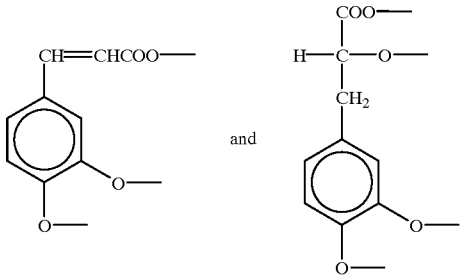

2. A method of claim 1, wherein the active agent further comprises D-(2,3-dihydroxyphenyl)lactic acid, rosemarinic acid, 2-(3,4-dihydroxyphenylethenyl)caffeic acid, lithospermate B, magnesium lithospermate B, a conjugation product of rosemarinic acid and 2-(3,4-dihydroxyphenylethenyl) caffeic acid, a dimer of 2-(3,4-dihydroxyphenylethenyl) caffeic acid, conjugated derivatives of said active agents.

3. A method of claim 1, wherein the infection is caused by a retrovirus.

4. A method of claim 1, wherein the composition is administered intranasally.

5. A method of claim 1, wherein the active agent is administered orally.

6. A method of claim 1, wherein the active agent is administered transdermally.

7. A method of claim 3, wherein the retrovirus is HIV.

8. A method of claim 3, wherein the retrovirus is FIV.

9. A method of claim 1, wherein the viral infection is caused by a virus that produces integrase or an integration protein.

10. A method of claim 1, wherein the active agent is administered parenterally.

11. A method of claim 1, wherein the active agent is administered intrathecally.

12. The method of claim 1, wherein at least one of the moieties is part of a dimer.

13. The method of claim 1, wherein both moieties are part of dimers.

14. The method of claim 1, wherein at least one of the moieties is part of a polymer.

* * * * *